United States Patent

Timms et al.

[11] Patent Number: 4,720,498
[45] Date of Patent: Jan. 19, 1988

[54] 2-ALKYL-THIOERGOLINES AND THEIR USE FOR TREATING ANXIETY

[75] Inventors: Graham H. Timms, Camberley; David E. Tupper, Reading, both of United Kingdom

[73] Assignee: Lilly Industries Limited, London, England

[21] Appl. No.: 791,856

[22] Filed: Oct. 28, 1985

[30] Foreign Application Priority Data

Oct. 31, 1984 [GB] United Kingdom ............... 8427536

[51] Int. Cl.$^4$ .................... A61K 31/48; C07D 457/02
[52] U.S. Cl. ........................................ 514/288; 546/67
[58] Field of Search ............................ 546/67, 68, 69; 514/288

[56] References Cited

U.S. PATENT DOCUMENTS

| | | | |
|---|---|---|---|
| 3,029,243 | 4/1962 | Olin | 546/67 |
| 3,901,894 | 8/1975 | Kornfeld et al. | 260/285.5 |
| 4,229,450 | 10/1980 | Ferrari et al. | 424/248.52 |
| 4,382,940 | 5/1983 | Bernardi et al. | 546/67 |

FOREIGN PATENT DOCUMENTS

160842 11/1985 European Pat. Off. .

OTHER PUBLICATIONS

Derwent 80235A/45, Abstracting Belgian 868,768.
Derwent 64222W/39, Abstracting DT 2,509,471.
Derwent 20614C/12, Abstracting EPO 8,802.

Primary Examiner—Donald G. Daus
Assistant Examiner—Cecilia Shen
Attorney, Agent, or Firm—Robert A. Conrad; Leroy Whitaker

[57] ABSTRACT

There is described a compound of the formula

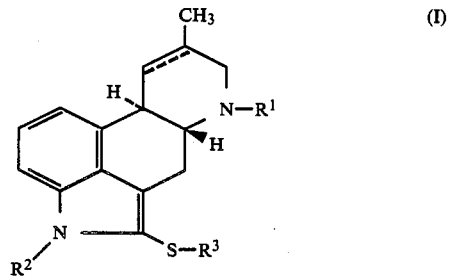

in which $R^1$ is hydrogen or $C_{1-4}$ alkyl, $R^2$ is hydrogen, $C_{1-4}$ alkyl, hydroxy $C_{1-4}$ alkyl, $C_{1-4}$ alkoxy $C_{1-4}$ alkyl, $HSC_{1-4}$ alkyl, $C_{1-4}$ alkyl-S-$C_{1-4}$ alkyl, $C_{1-4}$ alkylthio, optionally substituted arylthio or optionally substituted aralkylthio, and $R^3$ is hydrogen, $C_{1-4}$ alkyl, optionally substituted aryl or optionally substituted aralkyl; and salts thereof. The compounds show useful effects on the central nervous system.

7 Claims, No Drawings

2-ALKYL-THIOERGOLINES AND THEIR USE FOR TREATING ANXIETY

This invention relates to novel ergoline derivatives and their use as pharmaceuticals.

The literature describes many compounds having the basic ergoline structure

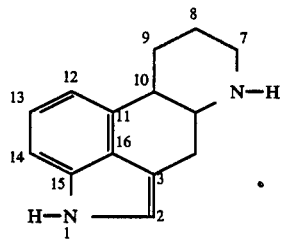

and such compounds have been found to possess a surprising variety of pharmaceutical activities. For example amides of lysergic acid have varied pharmacological properties and ergotamine has been used in the treatment of migraine, whereas ergocornine has been shown to be an inhibitor of prolactin and of tumours in rats. Non-peptide ergot derivatives, both naturally-occurring and synthetic, share these varied properties and compounds of this type have been shown to be useful in preventing pregnancy in animals, and to have anti-fertility and anti-lactating effects.

The present invention provides a group of novel compounds having the following general formula

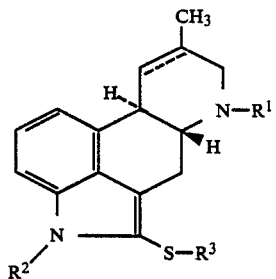

(I)

in which $R^1$ is hydrogen or $C_{1-4}$ alkyl, $R^2$ is hydrogen, $C_{1-4}$ alkyl, hydroxy $C_{1-4}$ alkyl, $C_{1-4}$ alkoxy $C_{1-4}$ alkyl, $HSC_{1-4}$ alkyl, $C_{1-4}$ alkyl-S-$C_{1-4}$ alkyl, $C_{1-4}$ alkylthio, optionally substituted arylthio or optionally substituted aralkylthio, and $R^3$ is hydrogen, $C_{1-4}$ alkyl, optionally substituted aryl or optionally substituted aralkyl; and salts thereof. The dotted line in the above chemical structure indicates an optional additional bond. These compounds show useful effects on the central nervous system.

When reference is made to $C_{1-4}$ alkyl this can be a straight or branched chain group and examples include methyl, ethyl, propyl, isopropyl, butyl or tert.butyl. Preferred alkyl groups are methyl and ethyl. Such alkyl groups can, in the case of a $R^2$ group be substituted with a hydroxy, $C_{1-4}$ alkoxy, HS- or $C_{1-4}$ alkyl S-substitutent. A $C_{1-4}$ alkoxy group is of the type RO- where R is a $C_{1-4}$ alkyl group such as defined above and a $C_{1-4}$ alkyl-thio group of the type RS- where R is $C_{1-4}$ alkyl. In the case of both $C_{1-4}$ alkoxy and $C_{1-4}$ alkylthio the alkyl moiety is preferably methyl or ethyl and preferred groups are $RO(CH_2)_2-$ and $RS(CH_2)_2-$ where R is methyl or ethyl.

$R^1$ is preferably $C_{1-4}$ alkyl, especially methyl, and $R^2$ is preferably hydrogen. $R^3$ is preferably $C_{1-4}$ alkyl, optionally substituted aryl or optionally substituted aralkyl, and is especially $C_{1-4}$ alkyl.

Optionally substituted aryl and arylalkyl groups comprise a phenyl group or a phenyl group substituted with one or more, preferably one to three, substituents selected from nitro, cyano, amino, hydroxyl, trifluoromethyl, $C_{1-4}$ alkyl, especially methyl, $C_{1-4}$ alkoxy, especially methoxy and ethoxy, and halogen especially fluorine, chlorine or bromine. Preferred substituents are $C_{1-4}$ alkyl, $C_{1-4}$ alkoxy and halogen. An arylalkyl group is preferably of the formula $Ph(CH_2)_n$ where n is 1 or 2.

It will be appreciated that general formula (I) covers three kinds of isomer. In the case of the compounds that are saturated at the 8,9 position, the methyl group in the 8-position can be directed axially or equitorially so that altogether three types of compound are embraced by the general formula. They can be regarded as derivatives of agroclavine, pyroclavine and festuclavine. The preferred compounds are those in which there is a double bond in the 8,9 position.

A preferred group of compounds of the invention are those having the agroclavine moiety of the following formula

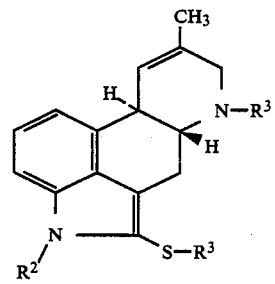

where $R^1$, $R^2$ and $R^3$ have the values given above. Preferably $R^1$ is $C_{1-4}$ alkyl, especially methyl, $R^2$ is hydrogen and $R^3$ is $C_{1-4}$ alkyl, especially methyl.

The novel compounds of the invention are useful both in their free base and acid addition salt forms. The acid addition salts are preferably the pharmaceutically acceptable, non-toxic addition salts with suitable acids, such as those with inorganic acids, for example hydrochloric, hydrobromic, nitric, sulphuric or phosphoric acids, or with organic acids, such as organic carboxylic acids, for example, glycollic, maleic, hydroxymaleic, fumaric, malic, tartaric, citric, salicylic, o-acetoxybenzoic, nicotinic or isonicotinic acid, or organic sulphonic acids for example methane sulphonic, ethane sulphonic, 2-hydroxyethane sulphonic, toluene-p-sulphonic, or naphthalene-2-sulphonic acid. Apart from pharmaceutically acceptable acid addition salts, other salts are also included within the scope of acid addition salts such as, for example, those with picric or oxalic acids; they may serve as intermediates in the purification of the compounds or in the preparation of other, for example pharmaceutically acceptable, acid addition salts, or are useful for identification, characterisation or purification of the bases.

The compounds of the invention can be readily prepared by reacting a compound of the formula

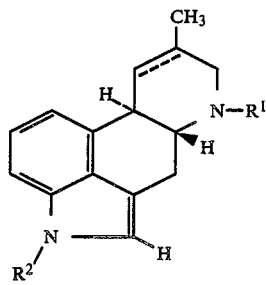

in which $R^1$ is hydrogen or $C_{1-4}$ alkyl and $R^2$ is hydrogen or $C_{1-4}$ alkyl, with a sulphenyl halide of the formula $R^3SY$ where Y is a halogen atom and $R^3$ is $C_{1-4}$ alkyl, optionally substituted aryl or optionally substituted aralkyl, optionally followed when it is desired to prepare a compound in which $R^2$ is hydroxy $C_{1-4}$ alkyl, $C_{1-4}$ alkoxy $C_{1-4}$ alkyl, $HSC_{1-4}$ alkyl or $C_{1-4}$ alkyl $SC_{1-4}$ alkyl, by reaction with the appropriate reagent.

Reaction with sulphenyl halide ($R^3SY$ where Y is halogen preferably chlorine) is preferably carried out in an inert organic solvent such as for example dichloromethene, at a temperature of for example from $-70°$ C. to $+25°$ C. When the reactant of formula (II) is one in which $R^2$ is hydrogen, reaction with sulphenyl halide results principally in the production of the compound in which $R^2$ is hydrogen and $R^3$ is $C_{1-4}$ alkyl, optionally substituted aryl or optionally substituted aralkyl, since substitution occurs preferentially at the 2-position. 1,2-Disubstitution also occurs especially when the reaction is carried out under basic conditions, for example in the presence of triethylamine.

When the compound to be prepared is one in which $R^2$ is hydroxy-$C_{2-4}$ alkyl, $C_{1-4}$ alkoxy $C_{1-4}$ alkyl, $HSC_{1-4}$ alkyl or $C_{1-4}$ alkyl $SC_{1-4}$ alkyl, the appropriate 2-substituted compound represented by

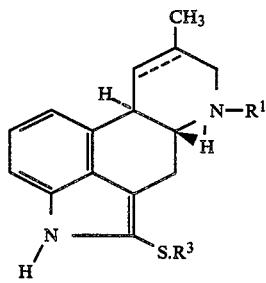

is reacted with a compound of formula $R^2Y$ where Y is halogen preferably chlorine. When $R^2$ is $HOCH_2$— the compound (III) is reacted with formaldehyde. The reaction is preferably carried out in an inert organic solvent such as for example tetrahydrofuran, preferably at a temperature of from $-10°$ C. to $+10°$ C. and in the presence of a base such as for example sodium hydride.

Compounds of formula (II) are either readily available, such as in the case of agroclavine, pyroclavine or festuclavine, or can be prepared by methods well-known in the art. For example, compounds in which $R^1$ is other than methyl can be prepared from agroclavine, pyroclavine or festuclavine by removal of the methyl group at the 6- position using trichloromethyl chloroformate followed by zinc/ethanol reduction, and subsequent alkylation. Similarly, alkyl substituents on the 1-position (compounds of formula (II) in which $R^2$ is $C_{1-4}$ alkyl) can be prepared by alkylation of the agroclavine, pyroclavine or festucalvine moiety.

Compounds of formula (I) in which $R^3$ is hydrogen can be prepared by special methods either by hydrolysing the 2-bromo substituted compound to give the corresponding amide derivative and reacting this with $P_2S_5$ or, alternatively, forming a compound of the formula

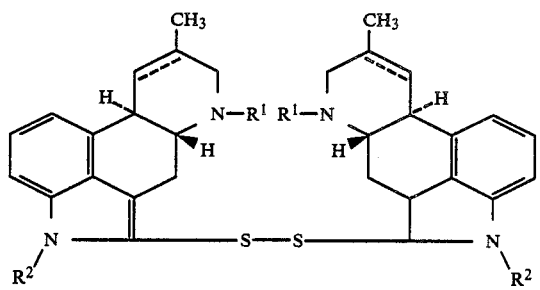

by reacting the unsubstituted compound with sulphur monochloride (CL-S-S-Cl), and cleaving this product with water at elevated temperature or by means of sodium borohydride.

As mentioned above, the compounds of the invention have useful central nervous system activity with low toxicity. This activity has been demonstrated in extensive testing in animal models using well-established procedures. More specifically the compounds have been shown to have activity in the spiroperidol binding test described by P. Seeman et al. in Nature 261, 717–719 (1976), and, for example, the compounds have an $IC_{50}$ value (the concentration of the compound required to reduce the binding of spiroperidol by 50%) of less than 5 $\mu M$. This test indicates that the compounds interact with dopamine receptors in the central nervous system and this is confirmed by their ability to alter serum prolactin levels and to change dopamine turnover. The compounds of formula (I) and pharmaceutically-acceptable acid addition salts thereof, are potent centrally acting compounds which are useful in the treatment of mild anxiety states, certain kinds of psychotic conditions such as schizophrenia and acute mania and parkinsonism.

The compounds are effective over a wide dosage range, the actual dose administered being dependent on such factors as the particular compound being used, the condition being treated and the type and size of mammal being treated. However, the dosage required will normally fall within the range of 0.05 to 10 mg/kg per day, for example in the treatment of adult humans dosages of from 0.2 to 5 mg/kg may be used.

The compounds and pharmaceutically-acceptable salts of the invention will normally be administered orally or by injection and, for this purpose, they will usually be utilised in the form of a pharmaceutical composition. Such compositions are prepared in a manner well known in the pharmaceutical art and normally comprise at least one active compound or pharmaceutically-acceptable salt of the invention associated with a pharmaceutically-acceptale carrier therefor. In making the compositions of the present invention, the active ingredient will usually be mixed with a carrier or diluted by a carrier, or enclosed within a carrier which may be in the form of a capsule, sachet, paper or other container. When the carrier serves as a diluent, it may be a solid, semi-solid or liquid material which acts as a vehicle, excipient or medium for the active ingredient. Some examples of suitable carriers are lactose, dextrose, sucrose, sorbitol, mannitol, starches, gum acacia, calcium phosphate, alginates, tragacanth, gelatin, syrup, methyl cellulose, methyl- and propyl-hydroxybenzoate, talc, magnesium stearate or mineral oil. The compositions of the invention may be formulated so as to provide quick, sustained or delayed release of the active ingredient after administration to the patient.

Depending on the route of administration, the foregoing compositions may be formulation as tablets, capsules or suspensions for oral use, injection solutions and subcutaneous implants. Preferably the compositions are formulated in a dosage unit form, each dosage containing from 1 to 300 mg, more usually 5 to 200 mg, of the active ingredient.

The invention is illustrated by the following Examples.

EXAMPLES 1 to 4

8,9-Didehydro-6,8-dimethyl-2-methylthioergoline

A solution of sulphuryl chloride (0.74 g,) in dichloromethane (15 ml) was added dropwise over 15 minutes at −20° C. to a stirred solution of dimethyl disulphide (0.46 g), in dichloromethane (15 ml). After allowing it to reach room temperature the solution of methyl sulphenyl chloride was added dropwise to a suspension of 8,9-didehydro-6,8-dimethylergoline (2.4 g) in dichloromethane (150 ml) at −70° C. The reaction mixture was stirred and allowed to reach room temperature overnight. Cold ammonia solution was added and the mixture extracted with dichloromethane (3×100 ml). The combined extracts were washed with water, dried ($MgSO_4$) and evaporated to dryness. Chromatography on neutral alumina ($CH_2Cl_2$) and crystallisation from cyclohexane gave the title compound, m.p. 148°–150° C. The mesylate was also prepared, m.p. 220°–222° C.

The following compounds were prepared by a similar method:

8,9-Didehydro-6-ethyl-8-methyl-2-methylthioergoline, m.p. 166°–168° C.

8,9-Didehydro-8-methyl-6-propyl-2-methylthioergoline, m.p. 173°–175° C.

8,9-Didehydro-6,8-dimethyl-2-n-propylthio ergoline mesylate, m.p. 181°–182° C.

EXAMPLE 5

8,9-Didehydro-6,8-dimethyl-2-ethylthioergoline

A solution of sulphuryl chloride (0.14 g), in anhydrous dichloromethane (10 ml) was added dropwise over fifteen minutes at −20° C. to a stirred solution of diethyldisulphide (0.67 g) in dichloromethane (10 ml). After stirring for ten minutes, the solution was added dropwise at 31 70° C. to 8,9-didehydro-6,8-dimethylergoline (2.4 g) in dichloromethane (100 ml). After allowing the solution to reach room temperature overnight, it was diluted with water, basified with concentrated ammonia solution (specific gravity 0.88) and extracted with dichloromethane three times. The combined dichloromethane extracts were washed ($H_2O$), dried ($MgSO_4$) and evaporated to give an oil (2.5 g). The oil was dissolved in a mixture of carbon tetrachloride and chloroform (1:1) and chromatographed over neutral alumina (grade III), eluting first with chloroform and then with ethyl acetate, to yield the purified product as an oil (2 g) which crystallised from isopropanol to give 8,9-didehydro-6,8-dimethyl-2-ethylthioergoline as light yellow needles, m.p. 168°–169° C.

EXAMPLE 6

8,9-Didehydro-6,8-dimethyl-1,2-di(1-methylethyl)thioergoline and
8,9-dihydro-6,8-dimethyl-2-(1-methylethyl)thioergoline Sulphuryl chloride (1.94 g) in dichloromethane (10 ml) was added dropwise at −5° C. to diisopropyldisulphide (2.2 g) in dichloromethane (10 ml). After stirring at room temperature for thirty minutes, the yellow solution was added dropwise at −20° C. to a solution of 8,9-didehydro-6,8-dimethylergoline (4.8 g) in dichloromethane (350 ml). After allowing the mixture to reach room temperature overnight, it was diluted with water, basified with concentrated ammonia solution (specific gravity 0.88) and extracted with dichloromethane three times. The combined dichloromethane extracts were washed ($H_2O$), dried ($MgSO_4$) and evaporated to give a black oil. The oil was dissolved in dichloromethane and chromatographed over neutral alumina (grade III) eluting first with dichloromethane to give the first product 8,9-didehydro-6,8-dimethyl 1,2-di(1-methylethyl)thioergoline (I), as an oil. (m.s. m/e 386)

Further elution with ethyl acetate yielded the second product 8,9-didehydro-6,8-dimethyl-2-(1-methylethyl)-thioergoline (II) as a yellow solid.

Product I (2 g) was dissolved in a solution of 5N HCl (50 ml) and ethanol (10 ml). After adding potassium iodide (1.33 g), the mixture was refluxed for one hour then diluted with water, basified with concentrated ammonia solution (specific gravity 0.88) and extracted with dichloromethane three times. The dichloromethane extracts were washed ($H_2O$), dried ($MgSO_4$) and evaporated to give a black oil. The oil was dissolved in ethyl acetate and chromatographed over neutral alumina (grade III) eluting with ethyl acetate to give a further sample of II as a yellow solid.

The two batches of II were combined and recrystallised from acetonitrile to give 8,9-didehydro-6,8-dimethyl 2-(1-methylether)thioergoline as yellow needles, m.p. 145°–147° C.

EXAMPLE 7

8,9-Didehydro-6,8-dimethyl-2-hexylthioergoline, hemifumarate

A solution of sulphuryl chloride (1.36 g) in dichloromethane (20 ml) was added dropwise over fifteen minutes at room temperature to a stirred solution of dihexyldisulphide (2.36 g) in dichloromethane (28 ml). After one hour, the solution was added dropwise under nitrogen at −10° C. to a stirred solution of 8,9-didehydro6,8-dimethylergoline (4.8 g) in dichloromethane (300 ml). After allowing the mixture to reach room temperature overnight, it was diluted with water, basified with concentrated ammonia solution (specific gravity 0.88) and extracted with dichloromethane three times. The combined dichloromethane extracts were washed ($H_2O$), dried ($MgSO_4$) and evaporated to give an oil (5 g). The oil was dissolved in dichloroemethane and chromatographed over neutral alumina (grade III), eluting first with dichloromethane and then with ethyl acetate, to yield the purified product as an oil (2.5 g). The oil was dissolved in ethanol, and a solution of fumaric acid (0.85 g) in ethanol was added to yield 8,9-didehydro-6,8-dimethyl-2-hexylthioergoline, hemifumarate as white crystals, m.p. 199°–201° C.

EXAMPLE 8

2-Benzylthio-8,9-didehydro-6,8-dimethyl ergoline

A solution of sulphuryl chloride (0.78 g) in dichloromethane (15 ml) was added dropwise to a stirred solution of dibenzyl disulphide (1.355 g) in dichloromethane (30 ml) at −20° C. After stirring at room temperature for 0.5 hours, the solution was added to 8,9-didehydro-6,8-dimethylergoline (2.38 g) in dichloromethane (200 ml) at −50° C. After the addition, and stirring the solution at −50° C. for one hour, the reaction mixture was allowed to come to room temperature overnight. The solution was diluted with water, basified with concentrated ammonia solution (0.88) and extracted with chloroform several times. The combined organic extracts were washed with water, dried over anhydrous magnesium sulphate and evaporated to give an oil. Column chromatography on neutral alumina (120 g), eluting with dichloromethane, then 5% methanol-dichloroemethane, gave 2-benzylthio-8,9-didehydro-6,8-dimethyl ergoline which was recrystallised from cyclohexane, m.p. 134°–136° C.

EXAMPLE 9 to 12

8,9-Didehydro-6,8-dimethyl-2-(4-methoxyphenyl)thioergoline

An ice cold solution of carbon tetrachloride (50 ml) was saturated with chlorine gas and then a solution of p-methoxybenzenethiol (1.35 ml), in carbon tetrachloride (10 ml) was added dropwise with stirring. After 10 minutes, the solvent and excess chlorine were removed in vacuo. The deep red oil was taken up in a small volume of dichloromethane and added dropwise to a stirred solution of 8,9-didehydro-6,8dimethylergoline (2.36 g) in dichloromethane (200 ml) at −20° C. After allowing the reaction mixture to come to room temperature overnight, it was diluted with ice-water, basified with concentrated ammonia solution (0.88) and the product extracted several times with chloroform. The organic fractions were then washed with water, dried over magnesium sulphate, filtered and the solvent removed in vacuo to give an oil. Column chromatography on a dry column of neutral alumina (120 g) eluting with 3% methanol/dichloromethane to yield a white solid as product which was recrystallised from isopropanol to give 8,9-didehydro-6,8-dimethyl-2-(4-methoxyphenyl)thioergoline, m.pl 202°–204° C.

The following compounds were similarly prepared:
- 8,9-Didehydro-6,8-dimethyl-2-phenylthioergoline mesylate, from phenyl sulphenyl chloride (prepared by the action of chlorine gas on benzene thiol) and 8,9-didehydro-6,8-dimethylergoline, m.p. >250° C. with decomposition (ex EtOH-Et$_2$O)
- 2-(4-chlorophenyl)thio-8,9-didehydro-6,8-dimethylergoline, from p-chlorophenyl sulphenyl chloride (from the action of chlorine gas on p-chlorothiophenol) and 8,9-didehydro-6,8-dimethylergoline, m.p. 162°–163° C. (ex cyclohexane)
- 6,8β-Dimethyl-2-phenylthioergoline mesylate, from phenyl sulphenyl chloride (prepared by the action of chlorine gas on benzene thiol) and 6,8β-dimethylergoline, m.p. 156°–158° C. (EtOH-Et$_2$O.

EXAMPLE 13

8,9-Didehydro-2-(4-fluorophenyl)thio-6,8-dimethylergoline mesylate

A solution of p-fluorothiophenol (2.82 g) in benzene (20 ml) was added slowly with ice-cooling to a stirred solution of N-chlorosuccinimide (2.94 g). A yellow colouration developed after five minutes which gradually went orange. After the addition was complete, the solution was stirred at room temperature overnight, was then filtered and the solvent removed to leave a red oil. Carbon tetrachloride was added to remove the last traces of succinimide and after filtration, the solvent removed in vacuo. The oil was taken up again in dichloromethane (15 ml) and added to a sirred solution of 8,9-didehydro-6,8-dimethylergoline (4.8 g) in dichloromethane (300 ml) at −70° C. After one hour at room temperature no starting material was left and iced-water was added. After basification with ammonia solution (specific gravity 0.88), the product was extracted several times with dichloromethane, the organic fractions collected and washed with water. After drying over anhydrous magnesium sulphate and filtration, the solution was evaporated in vacuo to give a solid which was recrystallised from isopropanol, m.p. 208°–209° C.

The mesylate was also prepared, m.p. >260° C. with decomposition.

EXAMPLE 14

6,8β-Dimethyl-2-methylthioergoline

A solution of sulphuryl chloride (1.48 g), in dichloromethane (20 ml) was added dropwise over fifteen minutes at −20° C. to a stirred solution of dimethyl disulphide (0.94 g) in dichloromethane (20 ml). After allowing to reach room temperature, the solution was added dropwise at −70° C. to a suspension of 6,8β-dimethylergoline (4.8 g) in dichloromethane (300 ml). The reaction mixture was maintained at −70° C. for ninety minutes and allowed to reach room temperature overnight to produce a black suspension. The mixture was diluted with water, basified with concentrated ammonia solution (specific gravity 0.88) and extracted with dichloromethane three times. The combined dichloromethane extracts were washed (H$_2$O), dried (MgSO$_4$) and evaporated to give white solid. The solid was dissolved in ethyl acetate and chromatographed over Florisil (250 g), eluting with ethyl acetate, to yield the purified product as a white solid which was recrystalised from ethanol to give 6,8β-dimethyl-2-methylthioergoline as white crystals, m.p. 201°–202° C.

EXAMPLES 15 to 18

8β-Methyl-6-propyl-2-methylthioergoline

A solution of sulphuryl chloride (0.74 g) in dichloromethane (15 ml) was added dropwise over 15 minutes at −20° C. to a stirred solution of dimethyl disulphide (0.46 g) in dichloromethane (15 ml). After allowing it to reach room temperature the solution of ethyl sulphenyl chloride was added dropwise to a suspension of 8β-methyl-6-propylergoline (2.4 g), in dichloromethane (150 ml) at −70° C. The reaction mixture was stirred and allowed to reach room temperature overnight. Ice cold ammonia solution was added and the mixture extracted with dichloromethane (3×100 ml). The combined extracts were washed with water, dried (MgSO$_4$) and evaporated to dryness. Chromatography on neutral alumina (CH$_2$CH$_2$) and crystallisation from ethanol gave the title compound. The free base was converted to its maleate salt and crystallised from ethanol, m.p. 216°–219° C.

The following compounds were similarly prepared:
6,8β-Dimethyl-2-propylthio ergoline maleate, using n-propyl sulphenylchloride (from propyl disulphide and sulphuryl chloride) and 6,8β-dimethylergoline, m.p. 162°–164° C. 6,8α-Dimethyl-2-methylthio ergoline maleate, from methyl sulphenyl chloride (from methyl disulphide and sulphuryl chloride) and 6,8α-dimethylergoline, m.p. 195°–198° C. 6,8α-Dimethyl-2-phenylthio ergoline maleate, from phenyl sulphenyl chloride (from phenyl disulphide and sulphuryl chloride) and 6,8α-dimethylergoline, m.p. 215°–217° C.

EXAMPLE 19

8,9-Didehydro-6,8-dimethyl-1-hydroxymethyl-2-methylthioergoline

A solution of 8,9-didehydro-6,8-dimethyl-2-methylthio ergoline (see Example 1) (2.84 g) in aqueous formaldehyde (40%, 35 ml) was refluxed for 2 hours. On cooling, water (100 ml) was added and the solution extracted several times with ethyl acetate. The organic extracts were collected, washed with water, dried over anhydrous magnesium sulphate and the solution filtered. It was reduced in vacuo to give a yellow oil which solidified on standing (2.2 g). This was passed through a dry neutral alumina column (100 g), eluting with chloroform and the final product, 8,9-didehydro-6,8-dimethyl-1-hydroxymethyl-2-methyl thioergoline recyrstallised from acetonitrile, m.p. 133°–135°.

EXAMPLE 20

8,9-Didehydro-2-methylthio-1,6,8-trimethyl ergoline

A solution of absolute ethanol (8 ml) in dry ether (10 ml) was added dropwise to a solution of sodium (1.68 g) in liquid ammonia (150 ml). The blue colour of the solution did not disappear. After 15 minutes, 8,9-didehydro-6,8-dimethyl-2-methylthio ergoline (see Example 1) (2.3 g) was added in portions. After a further 15 minutes, methyl iodide (2.52 ml) in ether (10 ml) was added dropwise over 10 minutes. The blue colour disappeared to give a clear solution which was left at room temperature overnight to given an orange solution. The residue was dissolve in dichloromethane and a saturated solution of sodium bicarbonate added. The aqueous phase was extracted several times with dichloromethane, the organic extract collected, washed with water, dried over anhydrous magnesium sulphate and the solvent removed in vacuo to give an oil (2.4 g). Column chromatography on neutral alumina (120 g) eluting with dichloromethane then chloroform gave a solid (1.5 g). Recrystallization from acetonitrile gave a colourless solid as 8,9-didehydro-2-methylthio-1,6,8-trimethyl ergoline, m.p. 115°–116° C.

EXAMPLE 21

8,9-Didehydro-8-methyl-2-methylthio ergoline

To a solution of 8,9-didehydro-6,8dimethyl-2-methylthio ergoline (11.36 g) in toluene (250 ml) that had been refluxed under Dean and Stark conditions for 0.5 hours to remove any trace of water and cooled, was added 2,2,2-trichloroethyl chloroformate (6 ml) and the solution refluxed under nitrogen overnight. After cooling and filtering through Celite, the solution was washed with 5N hydrochloric acid (3×50 ml), and water (3×50 ml). After drying the solution over magnesium sulphate and filtering, the solvent was removed in vacuo to leave a golden oil.

The oil was taken up in ethanol-acetic acid mixture (120 ml, 1:1) and zinc powder added in portions (40 g) at room temperature. After several hours the solution was filtered through Celite and water added (150 ml). The solution was washed several times with ether (3×50 ml) and then vasified with ammonia solution with cooling. The product was extracted with ethyl acetate (3×70 ml), washed with water (3×50 ml), dried over magnesium sulphate, filtered and the solvent removed under vacuo to give a pale yellow solid which recrystallised from ethanol, 177°–178° C.

The mesylate was also prepared, m.p. 260°–263° C., (ex EtOH) with decomposition.

The following Examples illustrate the preparation of typical formulations containing a solid active ingredient according to the invention.

EXAMPLE 22

Hard gelatin capsule
Each capsule contains

| Active ingredient | 10 mg |
|---|---|
| PEG 4000 | 250 mg |

The PEG 4000 is melted and mixed with the active ingredient. Whilst still molten the mixture is filled into capsule shells and allowed to cool.

EXAMPLE 23

Tablet
Each tablet contains

| Active ingredient | 10 mg |
|---|---|
| Calcium carbonate | 300 mg |
| Magnesium stearate | 10 mg |
| Starch | 30 mg |
| Hydroxypropylmethyl-cellulose | 10 mg |
| Iron oxide | 4 mg |

The active ingredient is granulated with calcium carbonate and starch. The dried granulate is blended with lubricant and disintegrant and compressed into tablets of the required dosage strength. The tablet may then be coated.

EXAMPLE 24

Injection

| Active ingredient | 10 mg |
|---|---|
| Water | 1 ml |

The active is dissolved in water and distributed into vials, ampoules or pre-pack syringes using appropriate equipment. The product is sterilised.

EXAMPLE 25

Controlled-Release Injection

| Active ingredient | 50 mg |
|---|---|
| Arachis oil | 2 ml |

The active is dissolved in the oil and distributed into vials, ampoules or pre-pack syringes. The product is sterilised.

EXAMPLE 26

Subcutaneous Implant

| Active ingredient | 250 mg |
|---|---|
| Poly (ε-caprolactone) | 4.75 g |

A solution of the active in a suitable solvent is added to the polymer, the mass moulded into appropriately-

We claim:
1. A compound of the formula

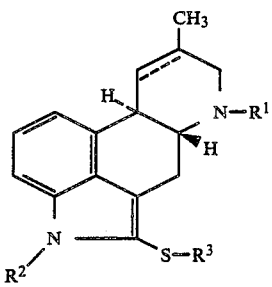

in which $R^1$ is hydrogen or $C_{1-4}$ alkyl, $R^2$ is hydrogen, $C_{1-4}$ alkyl, hydroxy $C_{1-4}$ alkyl, $C_{1-4}$ alkoxy $C_{1-4}$ alkyl, $HSC_{1-4}$ alkyl, $C_{1-4}$ alkyl-S-$C_{1-4}$ alkyl, $C_{1-4}$ alkylthio, or Ph—$(CH_2)_n$—S—, and $R^3$ is hydrogen, $C_{1-4}$ alkyl, or Ph—$(CH_2)_n$—, where n is 0-2 and each Ph is phenyl or phenyl substituted with a substituent selected from the group consisting of $C_{1-4}$ alkyl, $C_{1-4}$ alkoxy, and halo; and salts thereof.

2. A compound according to claim 1, in which $R^3$ is $C_{1-4}$ alkyl, or Ph—$(CH_2)_n$.

3. A compound according to claim 1 in which $R^1$ is $C_{1-4}$ alkyl, $R^2$ is hydrogen and $R^3$ is $C_{1-4}$ alkyl, or Ph—$(CH_2)_n$.

4. A compound of the formula

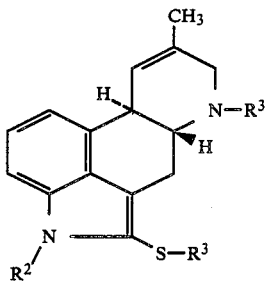

in which $R^1$ is $C_{1-4}$ alkyl, $R^2$ is hydrogen and $R^3$ is $C_{1-4}$ alkyl; and pharmaceutically-acceptable salts thereof.

5. 8,9-Didehydro-6,8-dimethyl-2-methylthioergoline, or a pharmaceutically-acceptable salt thereof.

6. A pharmaceutical formulation useful for treating an animal suffering from mild anxiety comprising an effective amount of a compound of formula (I) as defined in claim 1 or a pharmaceutically-acceptable salt thereof, in association with a pharmaceutically-acceptable carrier or diluent therefor.

7. A method of treating an animal, including a human, suffering from mild anxiety, which comprises administering an effective amount of a compound of formula (I) as defined in claim 1 or a pharmaceutically-acceptable salt thereof.